United States Patent
Tu et al.

(10) Patent No.: US 8,563,284 B2
(45) Date of Patent: Oct. 22, 2013

(54) **THERMOSTABLE *PAENIBACILLUS* XYLANASES**

(76) Inventors: Jenn Tu, Taipei (TW); Chun-Han Ko, Taipei (TW)

( * ) Notice: Subject to any disclaimer, the term of this patent is extended or adjusted under 35 U.S.C. 154(b) by 0 days.

(21) Appl. No.: 13/270,495

(22) Filed: Oct. 11, 2011

(65) Prior Publication Data

US 2012/0156734 A1    Jun. 21, 2012

Related U.S. Application Data

(60) Provisional application No. 61/391,260, filed on Oct. 8, 2010.

(51) Int. Cl.
*C12N 9/00* (2006.01)
*C12P 19/02* (2006.01)

(52) U.S. Cl.
USPC .......................................... 435/183; 435/105

(58) Field of Classification Search
None
See application file for complete search history.

*Primary Examiner* — Suzanne M Noakes

(57) ABSTRACT

This invention relates to mutant xylanases, nucleic acids encoding them, and methods of using these xylanases.

7 Claims, 9 Drawing Sheets

FIG. 1

```
                *         20         *         40         *         60
pre-XylX  :  MKIKKSFNVNKIEKTEFIAVLLFALVLFACSAQATTITSNEIGTHDGYDYSPWK :  60
XylX      :  ---------------------------------AQATTITSNEIGTHDGYDYSPWK :  31
XylX-s    :  -----------------------------CSAQATTITSNEIGTHDGYDYSPWK :  29
```

FIG. 2

```
              *        20         *        40         *        60
XylX-R   :  ............................................................ :  60
XylX-H1  :  ............................................................ :  60
XylX-H2  :  ............................................................ :  60
XylX-L1  :  ............................................................ :  60
XylX-L2  :  ............................................................ :  60
            MTMITPSLATTITSNEIGTHDGYDYSFWKDSGGSGSMTLNSGSTFSAQWSNINNILFKKG

*        80         *       100         *       120
XylX-R   :  ............................................................ : 120
XylX-H1  :  ............................................................ : 120
XylX-H2  :  ............................................................ : 120
XylX-L1  :  ............................................................ : 120
XylX-L2  :  ............................................................ : 120
            KKFNSTQSHQQIGNMSITYGAMFQDNGNAYLFVYGWTVDFLVEFYIVDSWGTYRFTGTNK

*       140         *       160         *       180
XylX-R   :  ............................................................ : 180
XylX-H1  :  ............................................................ : 180
XylX-H2  :  ............................................................ : 180
XylX-L1  :  ............................................................ : 180
XylX-L2  :  ............................................................ : 180
            GTINVDGSTYDIYSTTRVNQPSIKGTATFKQYWSVRTSKRTSGTISVSEHFRAWESRGMD

*       200         *       220         *       240
XylX-R   :  ............................................................ : 240
XylX-H1  :  ............................................................ : 240
XylX-H2  :  ............................................................ : 240
XylX-L1  :  ............................................................ : 240
XylX-L2  :  ............................................................ : 240
            MGKMYSVANTVRGYQSSGSANVYSNTLTIGGSNPGQSNPGSGTNPGTVTRVSASNMTKSG

*       260         *       280         *       300
XylX-R   :  ............................................................ : 300
XylX-H1  :  ............................................................ : 300
XylX-H2  :  ............................................................ : 300
XylX-L1  :  .....................................LALIVSHCS SSTHSTSDSYT----------- : 290
XylX-L2  :  ........................................S---------------------- : 270
            QYTGNISSPFNGVALYANNDSVEYTQYFSTSTHSFSLSGASNNANRARVDLKIGGQTKGT

*       320         *       340
XylX-R   :  ...................................... : 346
XylX-H1  :  ...................................... : 346
XylX-H2  :  ...................................-- : 344
XylX-L1  :  -------------------------------------- :   -
XylX-L2  :  -------------------------------------- :   -
            FYFGGSSPAVYTLNRVSHGTPNQETELIVIADDGTWDAYIDYLEIR
```

FIG. 7

DNA and amino acid sequences of xylX-H2

DNA sequence (SEQ ID NO:1)

ATGACCATGATTACGCCAAGCTTGGCAACAACGATCACTTCCAACGAGATTGGAACGCA
TGACGGTTATGACTATGAATTTTGGAAGGACAGCGGCGGTTCCGGCAGCATGACACTGA
ACAGCGGCGGTGCGTTCAGCGCTCAGTGGAGCAACATCAACAACATTCTGTTCCGCAAG
GGCAAAAAGTTCAATGAGACACAGACACATCAGCAAATCGGGAACATGTCGATCACCTA
CGGCGCCAACTTTCAGCCGAACGGCAATGCCTACTTAACCGTATACGGTTGGACGGTGG
ATCCGCTCGTTGAATTTTACATTGTCGACAGCTGGGGAACATACCGTCCGACAGGTACG
CATAAAGGAACCATTAACGTGGATGGCGGCACGTACGATATTTATGAGACGACCCGGT
GAACCAGCCATCGATTAAAGGAACGGCGACGTTCAAGCAGTATTGGAGTGTCCGGACGT
CGAAGCGAACGAGCGGTACGATCTCGGTCAGCGAGCATTTCAGAGCCTGGGAAAGCCGC
GGCATGCCGATGGGGAAAATGTATGAAGTCGCCATGACGGTAGAGGGCTATCAGAGCAG
CGGAAGCGCGAATGTGTACAGCAATACATTGACCATCGGCGGCGGCAACCCGGGCGGTG
GAAATCCGGGAGAAGGCACGAACCCGGGAACGGTGACGAGAGTCGAAGCCGAGAACATG
ACCAAAAGCGGGCAGTACACGGGCAATATCAGCTCGCCGTTCAATGGTGTTGCCCTGTA
TGCCAACAACGATTCGGTCAAATATACGCAGTATTTTTCACTAGTACTTATAGTTTCT
CACTGCGGGGCGTCGAACAATGCCAACATGGCCGTGGTGGACCTGAAGATCGGCGGC
CAGACGAAAGGCACCTTCTACTTTGGCGGAAGCAGTCCTGCGGTGTATACGCTAAACAA
TGTGAGTCATGGCACCGGCAATCAGGAGATTGAGCTGATTGTTACGGCGGATGACGGGA
CATGGGACGCCTACATTGACTATCTCGAG

Amino acid sequence (SEQ ID NO:2)

MTMITPSLATTITSNEIGTHDGYDYEFWKDSGGSGSMTLNSGGAFSAQWSNINNILFRK
GKKFNETQTHQQIGNMSITYGANFQPNGNAYLTVYGWTVDPLVEFYIVDSWGTYRPTGT
HKGTINVDGGTYDIYETTRVNQPSIKGTATFKQYWSVRTSKRTSGTISVSEHFRAWESR
GMPMGKMYEVAMTVEGYQSSGSANVYSNTLTIGGGNPGGGNPGEGTNPGTVTRVEAENM
TKSGQYTGNISSPFNGVALYANNDSVKYTQYFSTSTHSFSLRGASNNANMARVDLKIGG
QTKGTFYFGSSPAVYTLNNVSHGTGNQEIELIVTADDGTWDAYIDYLE

FIG. 8

DNA and amino acid sequences of xylX-H2 cloned in pET25b

DNA sequence
ATGACCATGATTACGCCAAGCTTGGCAACAACGATCACTTCCAACGAGATTGGAACGCA
TGACGGTTATGACTATGAATTTTGGAAGGACAGCGGCGGTTCCGGCAGCATGACACTGA
ACAGCGGCGGTGCGTTCAGCGCTCAGTGGAGCAACATCAACAACATTCTGTTCCGCAAG
GGCAAAAAGTTCAATGAGACACAGACACATCAGCAAATCGGGAACATGTCGATCACCTA
CGGCGCCAACTTTCAGCCGAACGGCAATGCCTACTTAACCGTATACGGTTGGACGGTGG
ATCCGCTCGTTGAATTTTACATTGTCGACAGCTGGGGAACATACCGTCCGACAGGTACG
CATAAAGGAACCATTAACGTGGATGGCGGCACGTACGATATTTATGAGACGACCCGGGT
GAACCAGCCATCGATTAAAGGAACGGCGACGTTCAAGCAGTATTGGAGTGTCCGGACGT
CGAAGCGAACGAGCGGTACGATCTCGGTCAGCGAGCATTTCAGAGCCTGGGAAAGCCGC
GGCATGCCGATGGGGAAAATGTATGAAGTCGCCATGACGGTAGAGGGCTATCAGAGCAG
CGGAAGCGCGAATGTGTACAGCAATACATTGACCATCGGCGGCGGCAACCCGGGCGGTG
AAAATCCGGAGAAGGCACGAACCCGGGAACGGTGACGAGAGTCGAAGCCGAGAACATG
ACCAAAAGCGGGCAGTACACGGGCAATATCAGCTCGCCGTTCAATGGTGTTGCCCTGTA
TGCCAACAACGATTCGGTCAAATATACGCAGTATTTTTCCACTAGCACTCATAGTTTCT
CACTGCGGGGGCGTCGAACAATGCCAACATGGCCCGGGTGGACCTGAAGATCGGCGGC
CAGACGAAAGGCACCTTCTACTTTGGCGGAAGCAGTCCCGCGGTGTATACGCTAAACAA
TGTGAGTCATGGCACCGGCAATCAGGAGATTGAGCTGATTGTTACGGCGGATGACGGGA
CATGGACGCCTACATTGACTATCTCGAGATCAAACGGGCTAGCCAGCCAGAACTCGCC
CCGGAAGACCCCGAGGATGTCGAGCACCACCACCACCACCACTGA

Amino acid sequence
MTMITPSLATTITSNEIGTHDGYDYFWKDSGGSGSMTLNSGGAFSAQWSNINNILFRK
GKKFNETQTHQQIGNMSITYGANFQPNGNAYLTVYGWTVDPLVEFYIVDSWGTYRPTGT
HKGTINVDGGTYDIYETTRVNQPSIKGTATFKQYWSVRTSKRTSGTISVSEHFRAWESR
GMPMGKMYEVAMTVEGYQSSGSANVYSNTLTIGGGNPGGGNPGEGTNPGTVTRVEAENM
TKSGQYTGNISSPFNGVALYANNDSVKYTQYFSTSTHSFSLRGASNNANMARVDLKIGG
QTKGTFYFGGSSPAVYTLNNVSHGTGNQEIELIVTADDGTWDAYIDYLEIKRASQPELA
PEDPEDVEHHHHHH

FIG. 9

DNA and amino acid sequences of xylX-H2 cloned in pET15b

DNA sequence

ATGGGCAGCAGCCATCATCATCATCATCACAGCAGCGGCCTGGTGCCGCGCGGCAGCCA
TATGACCATGATTACGCCAAGCTTGGCAACAACGATCACTTCCAACGAGATTGGAACGC
ATGACGGTTATGACTATGAATTTTGGAAGGACAGCGGCGGTTCCGGCAGCATGACACTG
AACAGCGGCGGTGCCGTTCAGTGCTTAGTGGAGCAACATCAACAACATTCTGTTCCGCAA
GGGCAAAAAGTTCAATGAGACACAGACACATCAGCAAATCGGGAACATGTCGATCACCT
ACGGCGCTAACTTTCAGTTGAACGGCAATGCCTACTTAACCGTATACGGTTGGACGGTG
GATCCGCTCGTTGAATTTTACATTGTCGACAGCTGGGGAACATACCGTCCGACAGGTAC
GCATAAAGGAACCATTAACGTGGATGGCGGCACGTACGATATTTATGAGACGACCCGGG
TGAACCAGCCATCGATTAAAGGAACGGCGACGTTCAAGCAGTATTGGAGTGTCCGGACG
TCAAGCGAACGAGCGGTACGATCTCGGTCAGCGAGCATTTCAGAGCTGGGAAAGCCG
CGGCATGCCGATGGGAAAATGTATGAAGTCGCCATGACGGTAGAGGGCTATCAGAGCA
GCGGAAGCGCGAATGTGTACAGCAATACATTGACCATCGGCGGCGGCAACCCGGGCGGT
GGAAATCCGGGAGAAGGCACGAACCCGGGAACGGTGACGAGAGTCGAAGCCGAGAACAT
GACCAAAAGCGGGCAGTACACGGGCAATATCAGCTCGCCGTTCAATGGTGTTGCCCTGT
ATGCCAACAACGATTCGGTCAAATATACGGCAGTATTTTTCCACTAGCACTCATAGTTTC
TCACTGCGGGGCGCTCGAACAATGCCAACATGGCCCGGGTGGACCTGAAGATCGGCGG
CCAGACGAAAGGCACCTTCTACTTTGGCGGAAGCAGTCCCGCGGTTGTATACGCTAAACA
ATGTGAGTCATGGCACCGGCAATCAGGAGATTGAGCTGATTGTTACGGCGGATGACGGG
ACATGGGACGCCTACATTGACTATCTCGAGGATCCGGCTGCTAACAAAGCCCGAAAGGA
AGCTGAGTTGGCTGCTGCCACCGCTGAGCAATAA

Amino acid sequence

MGSSHHHHHHSSGLVPRGSHMTMITPSLATTITSNEIGTHDGYDYEFWKDSGGSGSMTL
NSGGAFSAQWSNINNILFRKGKKFNETQTHQQIGNMSITYGANFQPNGNAYLTVYGWTV
DPLVEFYIVDSWGTYRPTGTHKGTINVDGGTYDIYETTRVNQPSIKGTATFKQYWSVRT
SKRTSGTISVSEHFRAWESRGMPMGKMYEVAMTVEGYQSSGSANVYSNTLTIGGGNPGG
GNPGEGTNPGTVTRVEAENMTKSGQYTGNISSPFNGVALYANNDSVKYTQYFSTSTHSF
SLRGASNNANMARVDLKIGGQTKGTFYFGGSSPAVYTLNNVSHGTGNQEIELIVTADDG
TWDAYIDYLEDPAANKARKEAELAAATAEQ

SEQUENCE LISTING

<160> NUMBER OF SEQ ID NOS: 16

<210> SEQ ID NO 1
<211> LENGTH: 1032
<212> TYPE: DNA
<213> ORGANISM: Paenibacillus campinasensis

<400> SEQUENCE: 1

```
atgaccatga ttacgccaag cttggcaaca acgatcactt ccaacgagat tggaacgcat      60
gacggttatg actatgaatt ttggaaggac agcggcggtt ccggcagcat gacactgaac     120
agcggcggtg cgttcagcgc tcagtggagc aacatcaaca acattctgtt ccgcaagggc     180
aaaaagttca atgagacaca gacacatcag caaatcggga acatgtcgat cacctacggc     240
gccaactttc agccgaacgg caatgcctac ttaaccgtat acggttggac ggtggatccg     300
ctcgttgaat tttacattgt cgacagctgg ggaacatacc gtccgacagg tacgcataaa     360
ggaaccatta acgtggatgg cggcacgtac gatatttatg agacgacccg ggtgaaccag     420
ccatcgatta aaggaacggc gacgttcaag cagtattgga gtgtccggac gtcgaagcga     480
acgagcggta cgatctcggt cagcgagcat ttcagagcct gggaaagccg cggcatgccg     540
atggggaaaa tgtatgaagt cgccatgacg gtagagggct atcagagcag cggaagcgcg     600
aatgtgtaca gcaatacatt gaccatcggc ggcggcaacc cgggcggtgg aaatccggga     660
gaaggcacga acccgggaac ggtgacgaga gtcgaagccg agaacatgac caaaagcggg     720
cagtacacgg gcaatatcag ctcgccgttc aatggtgttg ccctgtatgc caacaacgat     780
```

```
tcggtcaaat atacgcagta ttttccact agcactcata gtttctcact gcggggggcg    840
tcgaacaatg ccaacatggc ccgggtggac ctgaagatcg gcggccagac gaaaggcacc    900
ttctactttg gcggaagcag tcccgcggtg tatacgctaa acaatgtgag tcatggcacc    960
ggcaatcagg agattgagct gattgttacg gcggatgacg ggacatggga cgcctacatt    1020
gactatctcg ag                                                       1032
```

<210> SEQ ID NO 2
<211> LENGTH: 344
<212> TYPE: PRT
<213> ORGANISM: Paenibacillus campinasensis

<400> SEQUENCE: 2

```
Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
            20                  25                  30

Gly Ser Gly Ser Met Thr Leu Asn Ser Gly Gly Ala Phe Ser Ala Gln
        35                  40                  45

Trp Ser Asn Ile Asn Asn Ile Leu Phe Arg Lys Gly Lys Lys Phe Asn
    50                  55                  60

Glu Thr Gln Thr His Gln Gln Ile Gly Asn Met Ser Ile Thr Tyr Gly
65                  70                  75                  80

Ala Asn Phe Gln Pro Asn Gly Asn Ala Tyr Leu Thr Val Tyr Gly Trp
                85                  90                  95

Thr Val Asp Pro Leu Val Glu Phe Tyr Ile Val Asp Ser Trp Gly Thr
            100                 105                 110

Tyr Arg Pro Thr Gly Thr His Lys Gly Thr Ile Asn Val Asp Gly Gly
        115                 120                 125

Thr Tyr Asp Ile Tyr Glu Thr Thr Arg Val Asn Gln Pro Ser Ile Lys
    130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
            180                 185                 190

Gly Tyr Gln Ser Ser Gly Ser Ala Asn Val Tyr Ser Asn Thr Leu Thr
        195                 200                 205

Ile Gly Gly Gly Asn Pro Gly Gly Asn Pro Gly Glu Gly Thr Asn
    210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Thr Ser Thr
            260                 265                 270

His Ser Phe Ser Leu Arg Gly Ala Ser Asn Asn Ala Asn Met Ala Arg
        275                 280                 285

Val Asp Leu Lys Ile Gly Gly Gln Thr Lys Gly Thr Phe Tyr Phe Gly
    290                 295                 300

Gly Ser Ser Pro Ala Val Tyr Thr Leu Asn Asn Val Ser His Gly Thr
305                 310                 315                 320

Gly Asn Gln Glu Ile Glu Leu Ile Val Thr Ala Asp Asp Gly Thr Trp
                325                 330                 335
```

```
Asp Ala Tyr Ile Asp Tyr Leu Glu
            340

<210> SEQ ID NO 3
<211> LENGTH: 346
<212> TYPE: PRT
<213> ORGANISM: Paenibacillus campinasensis

<400> SEQUENCE: 3

Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
                20                  25                  30

Gly Ser Gly Ser Met Thr Leu Asn Ser Gly Gly Thr Phe Ser Ala Gln
            35                  40                  45

Trp Ser Asn Ile Asn Asn Ile Leu Phe Arg Lys Gly Lys Lys Phe Asn
    50                  55                  60

Glu Thr Gln Thr His Gln Gln Ile Gly Asn Met Ser Ile Thr Tyr Gly
65                  70                  75                  80

Ala Asn Phe Gln Pro Asn Gly Asn Ala Tyr Leu Thr Val Tyr Gly Trp
                85                  90                  95

Thr Val Asp Pro Leu Val Glu Phe Tyr Ile Val Asp Ser Trp Gly Thr
            100                 105                 110

Tyr Arg Pro Thr Gly Thr His Lys Gly Thr Ile Asn Val Asp Gly Gly
        115                 120                 125

Thr Tyr Asp Ile Tyr Glu Thr Thr Arg Val Asn Gln Pro Ser Ile Lys
    130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
            180                 185                 190

Gly Tyr Gln Ser Ser Gly Ser Ala Asn Val Tyr Ser Asn Thr Leu Thr
        195                 200                 205

Ile Gly Gly Gly Asn Pro Gly Gly Asn Pro Gly Glu Gly Thr Asn
    210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Thr Ser Thr
            260                 265                 270

His Ser Phe Ser Leu Arg Gly Ala Ser Asn Asn Ala Asn Met Ala Arg
        275                 280                 285

Val Asp Leu Lys Ile Gly Gly Gln Thr Lys Gly Thr Phe Tyr Phe Gly
    290                 295                 300

Gly Ser Ser Pro Ala Val Tyr Thr Leu Asn Asn Val Ser His Gly Thr
305                 310                 315                 320

Gly Asn Gln Glu Ile Glu Leu Ile Val Thr Ala Asp Asp Gly Thr Trp
                325                 330                 335

Asp Ala Tyr Ile Asp Tyr Leu Glu Ile Arg
            340                 345

<210> SEQ ID NO 4
```

```
<211> LENGTH: 346
<212> TYPE: PRT
<213> ORGANISM: Paenibacillus campinasensis

<400> SEQUENCE: 4

Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
            20                  25                  30

Gly Ser Gly Ser Met Thr Leu Asn Ser Gly Gly Ala Phe Ser Ala Gln
        35                  40                  45

Trp Ser Asn Ile Asn Asn Ile Leu Phe Arg Lys Gly Lys Lys Phe Asn
    50                  55                  60

Glu Thr Gln Thr His Gln Gln Ile Gly Asn Met Ser Ile Thr Tyr Gly
65                  70                  75                  80

Ala Asn Phe Gln Pro Asn Gly Asn Ala Tyr Leu Thr Val Tyr Gly Trp
                85                  90                  95

Thr Val Asp Pro Leu Val Glu Phe Tyr Ile Val Asp Ser Trp Gly Thr
            100                 105                 110

Tyr Arg Pro Thr Gly Thr His Lys Gly Thr Ile Asn Val Asp Gly Gly
        115                 120                 125

Thr Tyr Asp Ile Tyr Glu Thr Thr Arg Val Asn Gln Pro Ser Ile Lys
130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
            180                 185                 190

Gly Tyr Gln Ser Ser Gly Ser Ala Asn Val Tyr Ser Asn Thr Leu Thr
        195                 200                 205

Ile Gly Gly Asn Pro Gly Gly Asn Pro Gly Glu Gly Thr Asn
    210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Thr Ser Thr
            260                 265                 270

His Ser Phe Ser Leu Arg Gly Ala Ser Asn Asn Ala Asn Met Ala Arg
        275                 280                 285

Val Asp Leu Lys Ile Gly Gly Gln Thr Lys Gly Thr Phe Tyr Phe Gly
290                 295                 300

Gly Ser Ser Pro Ala Val Tyr Thr Leu Asn Asn Val Ser His Gly Thr
305                 310                 315                 320

Gly Asn Gln Glu Ile Glu Leu Ile Val Thr Ala Asp Gly Thr Trp
                325                 330                 335

Asp Ala Tyr Ile Asp Tyr Leu Glu Ile Arg
            340                 345

<210> SEQ ID NO 5
<211> LENGTH: 290
<212> TYPE: PRT
<213> ORGANISM: Paenibacillus campinasensis

<400> SEQUENCE: 5
```

```
Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
                20                  25                  30

Gly Ser Gly Ser Met Thr Leu Asn Ser Gly Gly Thr Phe Ser Ala Gln
            35                  40                  45

Trp Ser Asn Ile Asn Asn Ile Leu Phe Arg Lys Gly Lys Lys Phe Asn
        50                  55                  60

Glu Thr Gln Thr His Gln Gln Ile Gly Asn Met Ser Ile Thr Tyr Gly
65                  70                  75                  80

Ala Asn Phe Gln Pro Asn Gly Asn Ala Tyr Leu Thr Val Tyr Gly Trp
                85                  90                  95

Thr Val Asp Pro Leu Val Glu Phe Tyr Ile Val Asp Ser Trp Gly Thr
                100                 105                 110

Tyr Arg Pro Thr Gly Thr His Lys Gly Thr Ile Asn Val Asp Gly Gly
                115                 120                 125

Thr Tyr Asp Ile Tyr Glu Thr Thr Arg Val Asn Gln Pro Ser Ile Lys
            130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
                180                 185                 190

Gly Tyr Gln Ser Ser Gly Ser Ala Asn Val Tyr Ser Asn Thr Leu Thr
                195                 200                 205

Ile Gly Gly Asn Pro Gly Gly Asn Pro Gly Glu Gly Thr Asn
                210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Leu Ala Leu
                260                 265                 270

Ile Val Ser His Cys Gly Gly Arg Arg Thr Met Pro Thr Trp Pro Gly
                275                 280                 285

Trp Thr
    290

<210> SEQ ID NO 6
<211> LENGTH: 270
<212> TYPE: PRT
<213> ORGANISM: Paenibacillus campinasensis

<400> SEQUENCE: 6

Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
                20                  25                  30

Gly Ser Gly Ser Met Thr Leu Asn Ser Gly Gly Thr Phe Ser Ala Gln
            35                  40                  45

Trp Ser Asn Ile Asn Asn Ile Leu Phe Arg Lys Gly Lys Lys Phe Asn
        50                  55                  60

Glu Thr Gln Thr His Gln Gln Ile Gly Asn Met Ser Ile Thr Tyr Gly
65                  70                  75                  80
```

```
Ala Asn Phe Gln Pro Asn Gly Asn Ala Tyr Leu Val Tyr Gly Trp
                 85                  90                  95

Thr Val Asp Pro Leu Val Glu Phe Tyr Ile Val Asp Ser Trp Gly Thr
            100                 105                 110

Tyr Arg Pro Thr Gly Thr His Lys Gly Thr Ile Asn Val Asp Gly Gly
            115                 120                 125

Thr Tyr Asp Ile Tyr Glu Thr Thr Arg Val Asn Gln Pro Ser Ile Lys
        130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
            180                 185                 190

Gly Tyr Gln Ser Ser Gly Ser Ala Asn Val Tyr Ser Asn Thr Leu Thr
        195                 200                 205

Ile Gly Gly Asn Pro Gly Gly Asn Pro Glu Gly Thr Asn
    210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Arg
                260                 265                 270

<210> SEQ ID NO 7
<211> LENGTH: 60
<212> TYPE: PRT
<213> ORGANISM: Artificial sequence
<220> FEATURE:
<223> OTHER INFORMATION: Synthetic polypeptide

<400> SEQUENCE: 7

Met Lys Ile Tyr Gly Lys Arg Arg Asn Val Val Met Lys Thr Arg Lys
1               5                   10                  15

Lys Thr Arg Trp Phe Ile Ala Val Leu Leu Cys Phe Ala Leu Val Leu
            20                  25                  30

Pro Ala Gly Gly Ala Gln Ala Ala Thr Thr Ile Thr Ser Asn Glu Ile
        35                  40                  45

Gly Thr His Asp Gly Tyr Asp Tyr Glu Phe Trp Lys
    50                  55                  60

<210> SEQ ID NO 8
<211> LENGTH: 21
<212> TYPE: PRT
<213> ORGANISM: Artificial sequence
<220> FEATURE:
<223> OTHER INFORMATION: Synthetic polypeptide

<400> SEQUENCE: 8

Ala Thr Thr Ile Thr Ser Asn Glu Ile Gly Thr His Asp Gly Tyr Asp
1               5                   10                  15

Tyr Glu Phe Trp Lys
            20

<210> SEQ ID NO 9
<211> LENGTH: 29
<212> TYPE: PRT
<213> ORGANISM: Artificial sequence
<220> FEATURE:
```

<223> OTHER INFORMATION: Synthetic polypeptide

<400> SEQUENCE: 9

Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys
            20                  25

<210> SEQ ID NO 10
<211> LENGTH: 1107
<212> TYPE: DNA
<213> ORGANISM: Artificial sequence
<220> FEATURE:
<223> OTHER INFORMATION: Synthetic polynucleotide

<400> SEQUENCE: 10

```
atgaccatga ttacgccaag cttggcaaca acgatcactt ccaacgagat tggaacgcat      60
gacggttatg actatgaatt tggaaggac agcggcggtt ccggcagcat gacactgaac     120
agcggcggtg cgttcagcgc tcagtggagc aacatcaaca acattctgtt ccgcaagggc    180
aaaaagttca atgagacaca gacacatcag caaatcggga acatgtcgat cacctacggc    240
gccaactttc agccgaacgg caatgcctac ttaaccgtat acggttggac ggtggatccg    300
ctcgttgaat tttacattgt cgacagctgg ggaacatacc gtccgacagg tacgcataaa    360
ggaaccatta acgtggatgg cggcacgtac gatatttatg agacgacccg ggtgaaccag    420
ccatcgatta aggaacggc gacgttcaag cagtattgga gtgtccggac gtcgaagcga    480
acgagcggta cgatctcggt cagcgagcat ttcagagcct gggaaagccg cggcatgccg    540
atggggaaaa tgtatgaagt cgccatgacg gtagagggct atcagagcag cggaagcgcg    600
aatgtgtaca gcaatacatt gaccatcggc ggcggcaacc cgggcggtgg aaatccggga    660
gaaggcacga acccgggaac ggtgacgaga gtcgaagccg agaacatgac caaaagcggg    720
cagtacacgg gcaatatcag ctcgccgttc aatggtgttg ccctgtatgc caacaacgat    780
tcggtcaaat atacgcagta tttttccact agcactcata gtttctcact gcggggggcg    840
tcgaacaatg ccaacatggc ccgggtggac ctgaagatcg gcggcagac gaaaggcacc    900
ttctactttg gcggaagcag tcccgcggtg tatacgctaa acaatgtgag tcatggcacc    960
ggcaatcagg agattgagct gattgttacg gcggatgacg ggacatggga cgcctacatt   1020
gactatctcg agatcaaacg ggctagccag ccagaactcg ccccggaaga ccccgaggat   1080
gtcgagcacc accaccacca ccactga                                       1107
```

<210> SEQ ID NO 11
<211> LENGTH: 368
<212> TYPE: PRT
<213> ORGANISM: Artificial sequence
<220> FEATURE:
<223> OTHER INFORMATION: Synthetic polypeptide

<400> SEQUENCE: 11

Met Thr Met Ile Thr Pro Ser Leu Ala Thr Thr Ile Thr Ser Asn Glu
1               5                   10                  15

Ile Gly Thr His Asp Gly Tyr Asp Tyr Glu Phe Trp Lys Asp Ser Gly
            20                  25                  30

Gly Ser Gly Ser Met Thr Leu Asn Ser Gly Gly Ala Phe Ser Ala Gln
        35                  40                  45

Trp Ser Asn Ile Asn Asn Ile Leu Phe Arg Lys Gly Lys Lys Phe Asn
    50                  55                  60

-continued

Glu Thr Gln Thr His Gln Gln Ile Gly Asn Met Ser Ile Thr Tyr Gly
 65                  70                  75                  80

Ala Asn Phe Gln Pro Asn Gly Asn Ala Tyr Leu Thr Val Tyr Gly Trp
                 85                  90                  95

Thr Val Asp Pro Leu Val Glu Phe Tyr Ile Val Asp Ser Trp Gly Thr
            100                 105                 110

Tyr Arg Pro Thr Gly Thr His Lys Gly Thr Ile Asn Val Asp Gly Gly
        115                 120                 125

Thr Tyr Asp Ile Tyr Glu Thr Thr Arg Val Asn Gln Pro Ser Ile Lys
130                 135                 140

Gly Thr Ala Thr Phe Lys Gln Tyr Trp Ser Val Arg Thr Ser Lys Arg
145                 150                 155                 160

Thr Ser Gly Thr Ile Ser Val Ser Glu His Phe Arg Ala Trp Glu Ser
                165                 170                 175

Arg Gly Met Pro Met Gly Lys Met Tyr Glu Val Ala Met Thr Val Glu
            180                 185                 190

Gly Tyr Gln Ser Ser Gly Ser Ala Asn Val Tyr Ser Asn Thr Leu Thr
        195                 200                 205

Ile Gly Gly Asn Pro Gly Gly Asn Pro Gly Glu Gly Thr Asn
210                 215                 220

Pro Gly Thr Val Thr Arg Val Glu Ala Glu Asn Met Thr Lys Ser Gly
225                 230                 235                 240

Gln Tyr Thr Gly Asn Ile Ser Ser Pro Phe Asn Gly Val Ala Leu Tyr
                245                 250                 255

Ala Asn Asn Asp Ser Val Lys Tyr Thr Gln Tyr Phe Ser Thr Ser Thr
            260                 265                 270

His Ser Phe Ser Leu Arg Gly Ala Ser Asn Ala Asn Met Ala Arg
        275                 280                 285

Val Asp Leu Lys Ile Gly Gly Gln Thr Lys Gly Thr Phe Tyr Phe Gly
290                 295                 300

Gly Ser Ser Pro Ala Val Tyr Thr Leu Asn Asn Val Ser His Gly Thr
305                 310                 315                 320

Gly Asn Gln Glu Ile Glu Leu Ile Val Thr Ala Asp Asp Gly Thr Trp
                325                 330                 335

Asp Ala Tyr Ile Asp Tyr Leu Glu Ile Lys Arg Ala Ser Gln Pro Glu
            340                 345                 350

Leu Ala Pro Glu Asp Pro Glu Asp Val Glu His His His His His
        355                 360                 365

<210> SEQ ID NO 12
<211> LENGTH: 1155
<212> TYPE: DNA
<213> ORGANISM: Artificial sequence
<220> FEATURE:
<223> OTHER INFORMATION: Synthetic polynucleotide

<400> SEQUENCE: 12
atgggcagca gccatcatca tcatcatcac agcagcggcc tggtgccgcg cggcagccat      60
atgaccatga ttacgccaag cttggcaaca acgatcactt ccaacgagat tgaacgcat     120 gacggttatg actatgaatt ttggaaggac agcggcggtt ccggcagcat gacactgaac     180
agcggcggtg cgttcagcgc tcagtggagc aacatcaaca acattctgtt ccgcaagggc     240
aaaaagttca atgagacaca gacacatcag caaatcggga acatgtcgat cacctacggc     300
gccaactttc agccgaacgg caatgcctac ttaccgtgat acggttggac ggtggatccg     360
ctcgttgaat tttacattgt cgacagctgg ggaacatacc gtccgacagg tacgcataaa     420

```
ggaaccatta acgtggatgg cggcacgtac gatatttatg agacgacccg ggtgaaccag    480
ccatcgatta aaggaacggc gacgttcaag cagtattgga gtgtccggac gtcgaagcga    540
acgagcggta cgatctcggt cagcgagcat tcagagcct gggaaagccg cggcatgccg     600
atggggaaaa tgtatgaagt cgccatgacg gtagagggct atcagagcag cggaagcgcg    660
aatgtgtaca gcaatacatt gaccatcggc ggcggcaacc cgggcggtgg aaatccggga    720
gaaggcacga acccgggaac ggtgacgaga gtcgaagccg agaacatgac caaaagcggg    780
cagtacacgg gcaatatcag ctcgccgttc aatggtgttg ccctgtatgc caacaacgat    840
tcggtcaaat atacgcagta ttttttccact agcactcata gtttctcact gcggggggcg   900
tcgaacaatg ccaacatggc ccgggtggac ctgaagatcg gcggccagac gaaaggcacc    960
ttctactttg gcggaagcag tcccgcggtg tatacgctaa acaatgtgag tcatggcacc   1020
ggcaatcagg agattgagct gattgttacg gcggatgacg ggacatggga cgcctacatt   1080
gactatctcg aggatccggc tgctaacaaa gcccgaaagg aagctgagtt ggctgctgcc   1140
accgctgagc aataa                                                   1155
```

<210> SEQ ID NO 13
<211> LENGTH: 384
<212> TYPE: PRT
<213> ORGANISM: Artificial sequence
<220> FEATURE:
<223> OTHER INFORMATION: Synthetic polypeptide

<400> SEQUENCE: 13

```
Met Gly Ser Ser His His His His His His Ser Ser Gly Leu Val Pro
1               5                   10                  15

Arg Gly Ser His Met Thr Met Ile Thr Pro Ser Leu Ala Thr Thr Ile
            20                  25                  30

Thr Ser Asn Glu Ile Gly Thr His Asp Gly Tyr Asp Tyr Glu Phe Trp
        35                  40                  45

Lys Asp Ser Gly Gly Ser Gly Ser Met Thr Leu Asn Ser Gly Gly Ala
    50                  55                  60

Phe Ser Ala Gln Trp Ser Asn Ile Asn Asn Ile Leu Phe Arg Lys Gly
65                  70                  75                  80

Lys Lys Phe Asn Glu Thr Gln Thr His Gln Gln Ile Gly Asn Met Ser
                85                  90                  95

Ile Thr Tyr Gly Ala Asn Phe Gln Pro Asn Gly Asn Ala Tyr Leu Thr
            100                 105                 110

Val Tyr Gly Trp Thr Val Asp Pro Leu Val Glu Phe Tyr Ile Val Asp
        115                 120                 125

Ser Trp Gly Thr Tyr Arg Pro Thr Gly Thr His Lys Gly Thr Ile Asn
    130                 135                 140

Val Asp Gly Gly Thr Tyr Asp Ile Tyr Glu Thr Thr Arg Val Asn Gln
145                 150                 155                 160

Pro Ser Ile Lys Gly Thr Ala Thr Phe Lys Gln Tyr Trp Ser Val Arg
                165                 170                 175

Thr Ser Lys Arg Thr Ser Gly Thr Ile Ser Val Ser Glu His Phe Arg
            180                 185                 190

Ala Trp Glu Ser Arg Gly Met Pro Met Gly Lys Met Tyr Glu Val Ala
        195                 200                 205

Met Thr Val Glu Gly Tyr Gln Ser Ser Gly Ser Ala Asn Val Tyr Ser
    210                 215                 220

Asn Thr Leu Thr Ile Gly Gly Gly Asn Pro Gly Gly Gly Asn Pro Gly
```

```
                225                 230                 235                 240
Glu Gly Thr Asn Pro Gly Thr Val Thr Arg Val Ala Glu Asn Met
                245                 250                 255

Thr Lys Ser Gly Gln Tyr Thr Gly Asn Ile Ser Ser Pro Phe Asn Gly
                260                 265                 270

Val Ala Leu Tyr Ala Asn Asn Asp Ser Val Lys Tyr Thr Gln Tyr Phe
                275                 280                 285

Ser Thr Ser Thr His Ser Phe Ser Leu Arg Gly Ala Ser Asn Asn Ala
                290                 295                 300

Asn Met Ala Arg Val Asp Leu Lys Ile Gly Gly Gln Thr Lys Gly Thr
305                 310                 315                 320

Phe Tyr Phe Gly Gly Ser Ser Pro Ala Val Tyr Thr Leu Asn Asn Val
                325                 330                 335

Ser His Gly Thr Gly Asn Gln Glu Ile Glu Leu Ile Val Thr Ala Asp
                340                 345                 350

Asp Gly Thr Trp Asp Ala Tyr Ile Asp Tyr Leu Glu Asp Pro Ala Ala
                355                 360                 365

Asn Lys Ala Arg Lys Glu Ala Glu Leu Ala Ala Ala Thr Ala Glu Gln
                370                 375                 380

<210> SEQ ID NO 14
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 14
agcaagcttg gcaacaacga tcac                                              24

<210> SEQ ID NO 15
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 15
gcctctagat caccggatct cca                                               23

<210> SEQ ID NO 16
<211> LENGTH: 8
<212> TYPE: PRT
<213> ORGANISM: Artificial sequence
<220> FEATURE:
<223> OTHER INFORMATION: Synthetic peptide

<400> SEQUENCE: 16

Met Thr Met Ile Thr Pro Ser Leu
1               5
```

THERMOSTABLE *PAENIBACILLUS* XYLANASES

CROSS-REFERENCE TO RELATED APPLICATIONS

This application claims priority to U.S. Provisional Application No. 61/391,260, filed on Oct. 8, 2010, the content of which is incorporated herein by reference in its entirety.

BACKGROUND

Endo-1,4-β-xylanases (E.C.3.2.1.8) depolymerize xylan by random hydrolysis of the xylan backbone. Xylan is the second most common hemicellulose found in plant cell walls after cellulose. Recently, there has been much interest in using xylan and xylanases for various purposes, e.g., as a supplement in animal feed, for the manufacture of bread, food and drinks, in pulp and paper processing, and for the pretreatment of biomass conversions to produce bioethanol.

Although xylanases from thermophilic organisms are available, they may not be suitable for industrial processes. Thus, there is a need for mutant xylanases with improved enzyme activity and thermostability.

SUMMARY

This invention is based on, at least in part, the discovery of several mutant *Paenibacillus* xylanases with improved enzyme activity and thermostability. Accordingly, the present invention contemplates, inter alia, mutant xylanases, nucleic acids encoding them, and methods of using these xylanases.

In one aspect, described herein is an isolated polypeptide including an amino acid sequence that is at least 90% identical to the amino acid sequence of xylanase X-H2 (XylX-H2), i.e., SEQ ID NO:2. The polypeptide contains an Ala at a position that corresponds to residue 44 of SEQ ID NO:2 and a deletion of two amino acids that correspond to residues 345 and 346 of SEQ ID NO:2, and exhibits a lower optimal temperature and a higher specific activity as compared to a wild-type xylanase from *Paenibacillus campinasensis*. In some embodiments, the polypeptide includes SEQ ID NO: 2 with up to 50, e.g., 1, 10, 15, 20, 25, 30, and 45, conservative amino acid substitutions. The polypeptide can include the amino acid sequence of SEQ ID NO:2.

In another aspect, described herein is an isolated nucleic acid molecule having a nucleic acid sequence encoding a polypeptide comprising an amino acid sequence that is at least 90% identical to the amino acid sequence of SEQ ID NO:2, wherein the polypeptide includes an Ala at a position that corresponds to residue 44 of SEQ ID NO:2 and a deletion of two amino acids that correspond to residues 345 and 346 of SEQ ID NO:2, and wherein the polypeptide exhibits a lower optimal temperature and a higher specific activity as compared to a wild-type xylanase from *Paenibacillus campinasensis*. In some cases, the nucleic acid sequence of the nucleic acid molecule is SEQ ID NO:1.

The present invention also includes an expression vector containing the nucleic acid molecules described herein, and host cells having the expression vector.

In yet another aspect, the invention contemplates an isolated polypeptide including the amino acid sequence of a mutant xylanase, e.g., xylanase X-R (XylX-R), xylanase X-H1 (XylX-H1), xylanase X-L1 (XylX-L1), and xylanase X-L2 (XylX-L2).

Also included in this invention is a method of degrading xylan, the method including providing a xylanase polypeptide described herein, and mixing xylan and the polypeptide.

The details of one or more embodiments of the invention are set forth in the accompanying drawing and the description below. Other features, objects, and advantages of the invention will be apparent from the description and drawing, and from the claims.

BRIEF DESCRIPTION OF DRAWINGS

FIG. 1 is a scheme showing the N-terminal sequences of pre-XylX, XylX and XylX-R, i.e., SEQ ID NOs: 7, 8, and 9, respectively. Amino acid sequences shown here are the leading residues at the N-terminal of the proteins. The black-shaded sequence indicates the signal peptide of pre-XylX. The redundant residues at the N-terminal of XylX-R created by mutagenesis are shaded in gray.

FIG. 2 is an alignment of the amino acid sequences of XylX-R and other xylanase mutants, i.e., SEQ ID NOs: 2, 3 4, 5, and 6. The given amino acid sequence is the sequence of XylX-R (SEQ ID NO: 3). The shaded residues indicate changes as compared to the sequence of XylX-R.

FIG. 7 shows the nucleic acid sequence (SEQ ID NO:1) and the amino acid sequence (SEQ ID NO:2) of XylX-H2.

FIG. 8 shows the nucleic acid sequence and the amino acid sequence of XylX-H2 cloned in pET25b (XylX-H2 with a C-terminal 6xHis-tag), i.e., SEQ ID NOs: 10 and 11, respectively.

FIG. 9 shows the nucleic acid sequence and the amino acid sequence of XylX-H2 cloned in pET15b (XylX-H2 with a N-terminal 6xHis-tag), i.e., SEQ ID NOs: 12 and 13, respectively.

DETAILED DESCRIPTION

Figure 3:
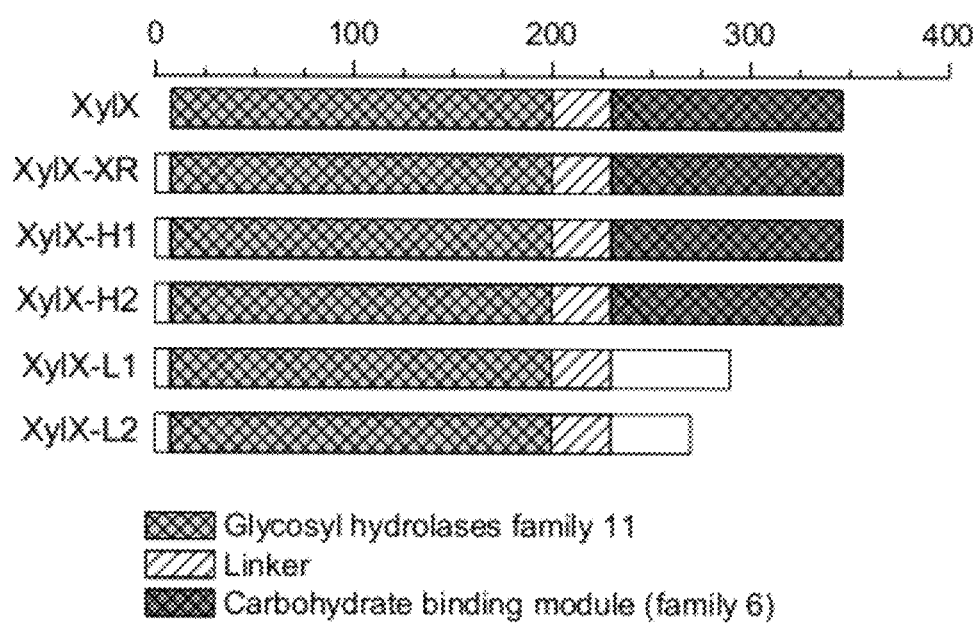
FIG. 3 is a schematic representation showing the functional domains of a wild-type xylanase, i.e., XylX, and various mutant xylanases. The catalytic domain of glycosyl hydrolase family 11 is connected to the carbohydrate-binding module family 6 with a proline-rich linker. XylX-L1 and XylX-L2 do not have a functional carbohydrate-binding domain. The scale on top indicates number of amino acid residues.

Described herein are, inter alia, five mutant xylanases derived from in vitro mutagenesis of the 41-kDa xylanase (XylX) from *Paenibacillus campinasensis* BL11. One of these mutants in particular, XylX-H2, possesses pH adaptability, thermostability and high specific activity. These characteristics render this xylanase suitable for a number of applications.

The present invention includes isolated xylanase polypeptides and their functional equivalents. FIG. 2 shows an alignment of the amino acid sequences of five xylanase mutants, i.e., XylX-R, XylX-H1, XylX-H2, XylX-L1 and XylX-L2. The amino acid sequence of XylX-H2 (SEQ ID NO: 2) is also shown in FIG. 7.

Functions or characteristics of a xylanase can include, for example, its enzymatic activity, its thermostability, its kinetic parameters, the temperature or range of temperatures at which it exhibits optimum activity (i.e., optimal temperature), and the pH or range of pHs at which it exhibits optimum activity. Those of ordinary skill in the art would be able to determine the functions and characteristics of a xylanase using methods known in the art and described below.

The term "isolated polypeptide" or "substantially purified polypeptide" used herein refers to a polypeptide substantially free from naturally associated molecules, i.e., the naturally associated molecules constituting at most 20% by dry weight of a preparation containing the polypeptide. Purity can be measured by any appropriate method, e.g., column chromatography, polyacrylamide gel electrophoresis, and HPLC.

The sequence identity of two amino acid sequences can be determined using the algorism described in Karlin and Altschul, Proc, Natl. Acad. Sci. USA 87:2264-2268, 1990, modified as described in Karlin and Altschul, Proc, Natl. Acad. Sci. USA 5873-5877, 1993. Such an algorism is incorporated into the NBLAST and XBLAST programs of Altschul et al., J. Mol. Biol. 215:403-410, 1990. BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al., Nucleic Acids Res. 25:3389-3402, 1997. When utilizing the BLAST and Gapped BLAST programs, the default parameters of the respective programs (e.g., XBLAST and NBLAST) are used. See the world wide web at ncbi.nlm.nih.gov.

The amino acid sequences of the polypeptides described herein may vary without disrupting the xylanase enzymatic activity of the polypeptides. For example, it can contain one or more conservative amino acid substitutions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in SEQ ID NO: 2, for example, is preferably replaced with another amino acid residue from the same side chain family. Alternatively, mutations can be introduced randomly along all or part of SEQ ID NO: 2, such as by saturation mutagenesis, and the resultant mutants can be screened for xylanase activity to identify mutants that retain the activity descried in the Example section below.

A polypeptide of the invention can be obtained as a synthetic polypeptide or a recombinant polypeptide. To prepare a recombinant polypeptide, a nucleic acid encoding it can be linked to another nucleic acid encoding a fusion partner, e.g., glutathione-s-transferase (GST), 6x-His epitope tag, or M13 Gene 3 protein. The resultant fusion nucleic acid expresses in suitable host cells a fusion protein that can be isolated by methods known in the art. The isolated fusion protein can be further treated, e.g., by enzymatic digestion, to remove the fusion partner and obtain the recombinant polypeptide of this invention.

This invention also contemplates the corresponding nucleic acid sequences that encode the mutant xylanase polypeptides described herein. In a preferred embodiment, the nucleic acid comprises the sequence of SEQ ID NO: 1 (which encodes SEQ ID NO: 2). A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of the vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention.

Also within the scope of this invention is a host cell that contains the above-described nucleic acid. Examples include E. coli cells, insect cells (e.g., using baculovirus expression vectors), yeast cells, plant cells, or mammalian cells. See e.g., Goeddel, (1990) Gene Expression Technology: Methods in Enzymology 185, Academic Press, San Diego, Calif. To produce a polypeptide of this invention, one can culture a host cell in a medium under conditions permitting expression of the polypeptide encoded by a nucleic acid of this invention, and purify the polypeptide from the cultured cell or the medium of the cell. Alternatively, the nucleic acid of this invention can be transcribed and translated in vitro, for example, using T7 promoter regulatory sequences and T7 polymerase.

This invention also contemplates compositions including the xylanase mutant polypeptides described herein and methods of using thereof. These compositions can be used in a variety of methods involving xylan degradation. For example, they can be employed 1) in biomass conversion by enzymatic breakdown of agricultural/forest wastes containing xylan for the pretreatment of bioethanol processing; 2) in improvement of in vivo breakdown of animal feeds and feed components containing xylan; 3) in bleaching pretreatment of pulp from plant fiber sources; 4) as baking agent; and 5) in any industrial processes involving xylan degradation.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are incorporated herein by reference in their entirety.

Example

The *Paenibacillus campinasensis* BL-11 strain was previously identified and isolated from a high temperature and alkaline environment. See, Ko et al., Bioresource Technol. 98: 2727-2733, 2007. An open reading frame (ORF) coding the 41-kDa endoxylanase (pre-XylX) from *Paenibacillus campinasensis* BL11 was cloned and expressed in *E. coli*; the ORF coding its endoglucanase was also identified. See, Ko et al., Bioresour Technol. 101: 7882-7888, 2010. The amino acid sequence of pre-XylX is only 73% identical to the next closest sequence found in the database. See, Ko et al., Process Biochem. 45: 1638-1644, 2010.

In this study, in vitro mutagenesis was carried out to improve the enzyme activity and thermostability of the 41-kDa xylanase that originated from *Paenibacillus campinasensis* BL11. A non-secretory intracellular xylansase, XylX-R, was created by directed mutagenesis. Using xylX-R as a template for error-prone PCR, four mutants were obtained after two stages of mutagenesis.

(1) Materials and Methods

All chemicals used were either from Sigma (St Louis, USA) or of analytical grade obtained from E. Merck (Darmstadt, Germany), unless specified otherwise. Bacteria were routinely cultured in Luria-Bertani (LB) medium. LB medium contained 10 g/L Bacto-tryptone, 5 g/L yeast extract, and 5 g/L NaCl. Vector pBCKS(+) and *E. coli* NM522 were from Stratagene (La Jolla, USA). Vectors pET15b, pET-25b and *E. coli* HMS174 (DE3) were from Novagen (Madison, USA). T-vector pOptima was from Strong Biotech (Taipei). PCR primers were synthesized by Bio Basic, Inc. (Markham, Ontario, Canada).

A three-step in vitro mutagenesis was carried out: (1) construction of a new open reading frame containing mature XylX only (lacking signal peptide) by directed mutagenesis PCR, (2) creation of a random mutation library of xylX by error-prone PCR, and (3) further directed mutagenesis to eliminate unnecessary parts of isolated mutants.

Template DNA used in the first and second rounds of PCR was an xylX-carrying pBCKS(+). See, Ko et al., Bioresour Technol. 101: 7882-7888, 2010. DNAs from mutants created in the second round was used as the templates in the third round of mutagenesis. The third round mutagenesis was operated in coordination with the construction of an expression system. The primer pair used for the first two rounds included X3shH-F (5'-AGCAAGCTTGGCAACAACGATCAC-3' (SEQ ID NO: 14); nucleotide sequence matching the N-terminal of XylX underlined) and X3shX-R (5'-GCCTCTA-GATCACCGGATCTCCA-3' (SEQ ID NO: 15); nucleotide sequence matching the C-terminal of XylX underlined).

For directed mutagenesis, a conventional PCR protocol was used. In error-prone PCR to create random mutations, a xylX mutant library was generated using Diversify PCR Random Mutagenesis Kit of Clontech (Palo Alto) according to the manufacturer's instructions. The PCR products were cloned into vector pOptima after purification with QIAquick purification kit (Qiagen, Hilden, Germany). Transformants were grown on LA (Luria-Bertani agar) master plates for further mutant screening.

Screening and isolation of XylX mutants were conducted following the protocols described previously with some modification. See, Ko et al., Bioresour Technol. 101: 7882-7888, 2010. NM522 transformants were selected on LA master plates containing ampicillin (100 μg/ml) at a density of about 50 to 100 colonies per 9-cm plate. After incubation at 37° C. overnight, a double replica on LA plates (2% of agar) containing oat spelt xylan (0.2%, w/v), ampicillin (100 μg/ml), D-cycloserine (100 μg/ml) and IPTG (isopropyl-β-D-thio-galactopyranoside, 1 mM) was made from each master plate. The replicas were incubated at 37° C. for 4 hours and heated at 65° C. for 30 minutes. Colonies on the replicas were lysed by spraying 0.1% Triton X-100 using an aerosol. After a 2-hour incubation at 65° C. to carry out the enzyme reaction, the replicas were stained with Congo red. See, e.g., Wood et al., Methods Enzymol. 160: 59-74, 1988. The clones showing more clearer zones were selected and checked to confirm the activities and sequences of the mutant xylanases.

The nucleotide sequences encoding the XylX mutants were determined by FS DNA polymerase fluorescent dye terminator reactions. Sequencing products were detected by using an Applied Biosystems 377 stretch automated sequencer (Applied Biosystems, Foster City, Calif., USA). Nucleotide sequences and their deduced amino acid sequences were analyzed with the Sequence Analysis tools of EMBL Computational Services (world wide web at ebi.ac.uk/Tools/sequence.html). Related sequences were obtained from searches in databases (i.e., SwissPort, PIR, PRF, and GenBank) using the programs BLASTP 2.0 and FASTA. The nucleic acid sequences of four xylX mutants, i.e., xylX-R, xylX-H1, xylX-L1 and xylX-L2, have been deposited in GenBank under accession Nos. HM630610, FJ168524, FJ168525 and HM630609, respectively.

The amino acid sequences encoded by the mutant genes were analyzed using various softwares. The predicted signal peptide and cleavage site were analyzed using NN (neural networks) and HMM (hidden Markov models) methods. Conserved domains were searched using InterProScan (EMBL EBI) and PSI-CD (NCBI). Finally, multiple alignments of the deduced amino acid sequences of the mutants with the sequences of XylX and pre-XylX were performed by ClustalW (EMBL-EBI). The Conserved Domain Search Service of NCBI was used for the analysis of functional enzyme domains. For simulation of the structures of the xylanases, SWISS-MODEL Workspace was used.

For gene expression in *E. coli*, the pET expression system of Novagen (Madison) was used. DNA fragments containing mutant sequences were amplified from the selected pOptima clones by PCR. The amplified products were subjected to digestion with Nde I and Xho I, and cloned into pET15b or pET25b and then used to transform *E. coli* strain HMS174 (DE3).

Expression and purification of XylX mutants were conducted following the protocols described previously. See, Ko et al., Bioresour Technol. 101: 7882-7888, 2010.

Standard xylanase assay was carried out by the dinitrosalicylic acid (DNSA) method using D-xylose as a standard. See, e.g., König et al, Anal. Bioanal. Chem. 37: 80-87, 2002. Briefly, the reaction mixture, which contained 30 μl of enzyme sample and 300 μl of 1.5% oat spelt xylan, was incubated at the designated temperature for 20 min at pH 7, 60° C. The reaction was terminated by adding 150 μl of DNSA (stop solution). The reaction mixture was then centrifugation and the supernatant was boiled. The boiled sample was then measured at OD$_{530}$. Enzyme activities (IUs) were calculated according to the aforementioned method. The buffer used was 100 mM phosphate buffer. The effect of temperature on the reaction was assessed by incubating the reaction mixtures at different temperatures in the range of 40 to 80° C. All the assays were carried out in triplicates.

Reactions were conducted at the optimal condition, i.e., pH 7 and 60° C., using 5 to 40 mg/mL oat spelt xylan solutions. Double reciprocal Lineweaver-Burk plots for xylanase activity versus substrate concentration were constructed to estimate kinetic parameters ($K_m$ and $V_{max}$) by linear regression for XylX-H2-25b and XylX-L2. $k_{cat}$ values were estimated by fitting a hyperbolic Michaelis-Menton equation using nonlinear regression with Sigma plot software ver. 10.0 (SPSS, Chicago).

(2) The Basic Backbone of the XylX Mutants: XylX-R

To ensure that all the mutations induced by error-prone PCR occurred in the mature enzyme, i.e., XylX, but not in the signal peptide of pre-XylX, an ORF containing only the coding sequence of XylX was constructed by directed mutagenesis. The resultant xylanase was designated as XylX-R. A comparison of the N-terminal sequences of XylX, pre-XylX and XylX-R is shown in FIG. 1. Structurally, the signal peptide (39 amino acids in length) of pre-XylX has been substituted by a short artificial peptide of 8 amino acids, i.e., MTMITPSL (SEQ ID NO: 16). XylX-R is a non-secretory intracellular enzyme. No enzyme activity was found in the culture milieu of the clones.

Rough estimates of the enzyme activities of XylX-R and XylX using crude preparation were carried out at 57.5° C. to 70° C. The results are summarized in Table 1 below. No significant differences in the activities of the enzymes could be found. Fusing an oligopeptide to the N-terminal of XylX did not have any significant effect on enzyme activity.

TABLE 1

Comparison of the enzyme activities of XylX-R and two XylXs at different temperatures.

| | Temperature (° C.) | | | | | |
|---|---|---|---|---|---|---|
| | 57.5 | 60 | 62.5 | 65 | 67.5 | 70 |
| pOptima-xylX-R | 804.03 | 1016.30 | 934.69 | 401.12 | 106.36 | 45.71 |
| pBCKS(+)-xylX | 932.59 | 1242.46 | 1091.99 | 547.11 | 170.31 | 41.89 |
| pOptima-xylX | 733.12 | 976.97 | 806.92 | 419.16 | 146.38 | 31.40 |

Enzyme activities are expressed by IU per mg of total proteins.

(3) Mutants with Improved Properties

Screening the mutant library created by error-prone PCR, two mutants with improved activities were obtained. One of the mutants was a missense (i.e., T44A) mutant, i.e., XylX-H1. The other was a deletion mutant, i.e., XylX-L1, caused by a deletion of a single nucleotide.

Deletion in the C-terminal of XylX (or XylX-R) resulted in an increase of enzyme activity, as described in more detail below. XylX-H2 was derived by deleting the two C-terminal amino acid residues of XylX-H1. XylX-L2 also includes a C-terminal deletion.

A comparison of the amino acid sequences of XylX-R, XylX-H1, XylX-H2, XylH- L1 and XylH- L2 is shown in FIG. 2. A diagram showing the functional domains of XylX and the mutants is shown in FIG. 3.

(4) Reaction Optima and Enzyme Activity

To evaluate the performance of the mutants, his-tagged enzymes were purified by Ni-NTA affinity chromatography. Activities of the purified enzymes were determined at different pHs and temperatures. The results are summarized in Table 2 below. The enzyme activities of XylX-R, XylX-H1, XylX-H2 and XylX-L1 were highest at 55° C. and pH 7. On the other hand, the reaction optima for XylX-L2 was at 50° C. and pH 8. The optimal temperatures for the mutants were about 5-10° C. lower than the wild-type enzyme. XylX-L1 and XylX-L2 were more alkaliphilic. The highest xylanase activity was exhibited by the recombinant xylanase expressed by xylX-H2 cloned into pET 25b, denoted as XylX-H2-25b in Table 2. The optimal activities of the mutants were higher then most of xylanases previously studied. See, Beg et al., Appl. Microbiol. Biotechnol. 56: 326-338, 2001; and Sá-Pereira et al., Mol. Biotechnol. 24(3): 257-81, 2003. The addition of 6xHis-tag to the C-terminus (the binding domain) rendered the xylanase activity of XylX-H2-25b almost three times higher then that of XylX-H2 with 6xHis-tag added to the N-terminus.

TABLE 2

Enzyme activities and reaction optimas of six different xylanases.

| | Reaction | Specific activity (U/mg)[a] | |
|---|---|---|---|
| Enzyme | optima | at 60° C., pH = 7 | at optimal condition |
| Xylanase X[b] | 60° C., pH 7 | 2392 | 2392 |
| Xylanase X-R[c] | 55° C., pH 7 | 2037 | 2243 |
| Xylanase X-H1[c] | 55° C., pH 7 | 2183 | 2618 |
| Xylanase X-H2[c] | 55° C., pH 7 | 3360 | 4766 |
| Xylanase X-L1[c] | 55° C., pH 7 | 3382 | 5399 |
| Xylanase X-L2[c] | 50° C., pH 8 | 2810 | 4710 |
| Xylanase-H2-25b | 55° C., pH 7 | 8494 | 9725 |

[a]specific activity: enzyme units/mg of purified enzyme.
[b]enzyme his-tagged at C-terminal.
[c]enzymes his-tagged at N-terminal.

The drop in the optimal temperatures of all mutants might be caused by the alteration in the N-terminus, and the shift in alkaliphilicity of XylX-L1 and XylX-L2 might be caused by the sequence deletion at the C-terminus. Compared to XylX-R, XylX-H1 showed about a 10% increase in activity, whereas XylX-L1 had a 50% increase. Remarkably, XylX-L2 and XylX-H2 showed activities that were two times or more higher than that of XylX-R and XylX. The 10% increase in the activity of XylX-H1 can be attributed to the T44A mutation. Note that another mutation at the same position (T44M) caused significant impairment of enzyme activity (data not shown). The mutant enzymes found in this study functioned well, with residual activities greater than 60% for more than 4 hours at between 45-65° C. in the pH range of 5-9 (data not shown).

Figure 4:
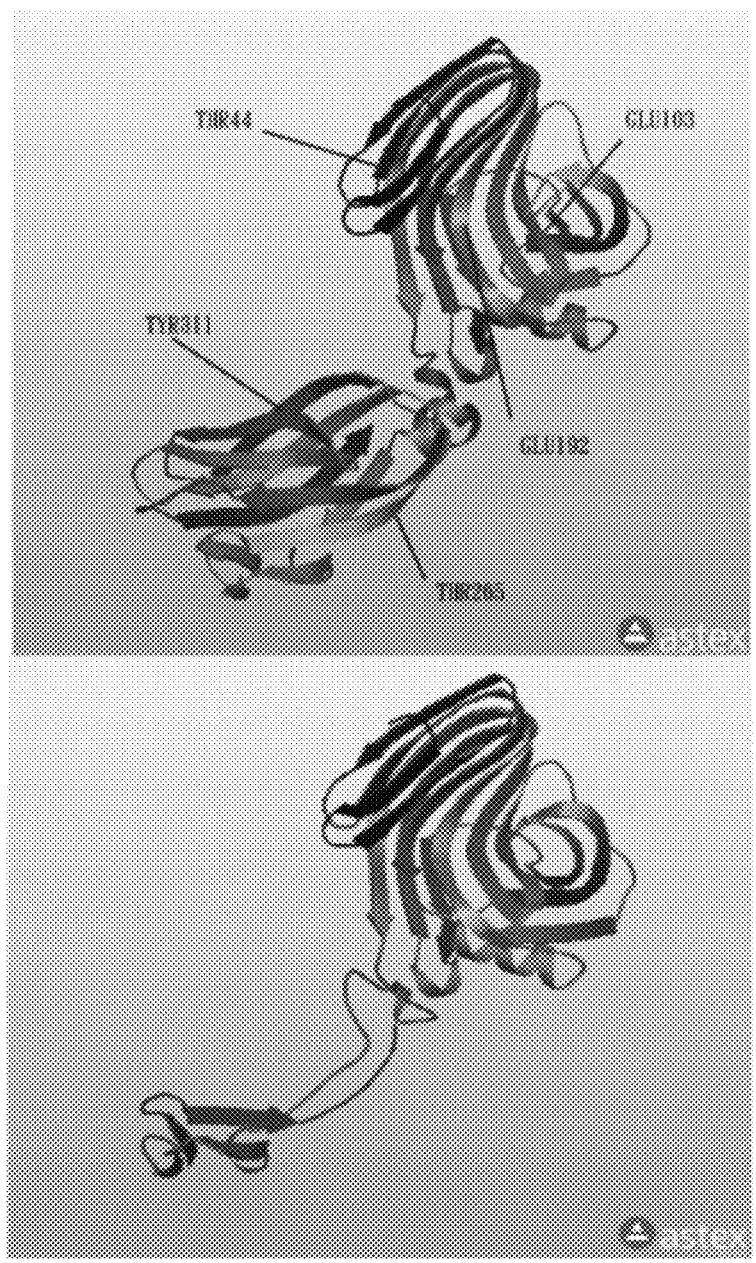
FIG. 4 depicts a simulation of the structures of XylX-R (top) and XylX-L2 (bottom) using SWISS-MODEL. Positions of residue Thr44, Glu103 and Glu192 are indicated.

The protein structure of the above-described mutants were simulated using SWISS-MODEL Workspace. The structures of XylX, XylX-R, XylX-H1 and XylX-H2 were nearly the same. Both XylX-L1 and XylX-L2 differed from them only as a result of a peptide sequence deletion. The structures of XylX-R and XylX-L2 are shown in FIG. 4.

(5) Effect of Temperature on the Stability of XylX-H2-25b and XylX-L2

Figure 5:
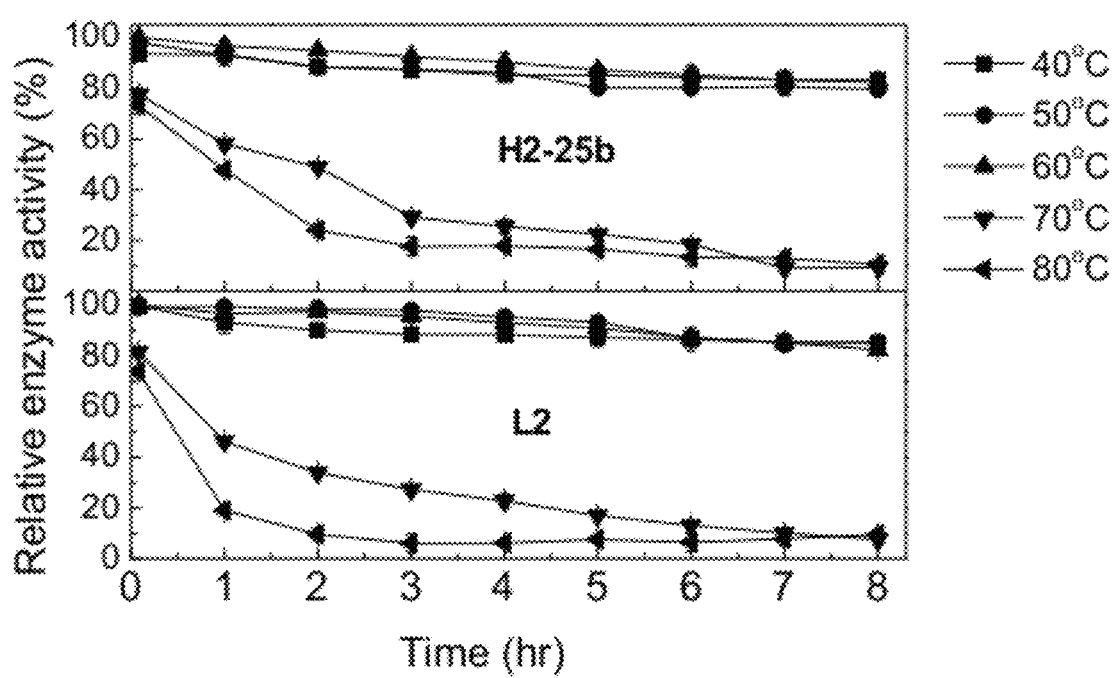
FIG. 5 is a graph showing the thermostability of XylX-H2-25b (top) and XylX-L2 (bottom) at pH 7.

The effect of temperature on the stability of XylX-H2-25b and XylX-L2 was investigated from 40° C. to 80° C. at pH 7. See FIG. 5. Xylanase activities of both mutants at pH 7 from 40° C. to 60° C. remained at more than 80% of their initial levels for 8 hours. At 70° C. and 80° C., the residual activities of both mutant xylanases were around 10% of their initial levels even after 8 hours. The half-lives from 40° C. to 60° C. were estimated by plotting the natural logarithms of residual activities against time, followed by linear regression. The half-lives from 40° C. to 60° C. for both mutants, listed in Table 3 below, were greater than those of most bacterial xylanases previously studied. See, Techapun et al., Process Biochem. 38: 1327-1340, 2003. The half-lives at 60° C. were more than 24 hours for both mutants. Even at 70° C. and 80° C., the interpolated half-lives of XylX-H2-25b were 96 and 36 minutes, respectively. For both mutants, the interpolated half-lives at 70° C. and 80° C. were higher than the values of the mutants derived from *Geobacillus stearothermophilus* xylanase. See, Zhang et al., Bioresource Technol. 101: 9272-9278, 2010. Excellent thermostability renders both mutants attractive candidates for biomass conversion, such as simultaneous saccharification and fermentation requiring long reaction times, and for other industrial applications conducted at higher temperatures.

TABLE 3

Half-lives of the xylanase mutants XylX-H2 and XylX-L2 at pH 7.

| Temp. (° C.) | t/2 (min) | |
|---|---|---|
| | H2 | L2 |
| 40 | 2472 | 2424 |
| 50 | 1488 | 1866 |
| 60 | 1656 | 1764 |
| 70 | 96 | 66 |
| 80 | 36 | 12 |

(6) Kinetic Parameters of XylX-H2 and XylX-L2

Figure 6:
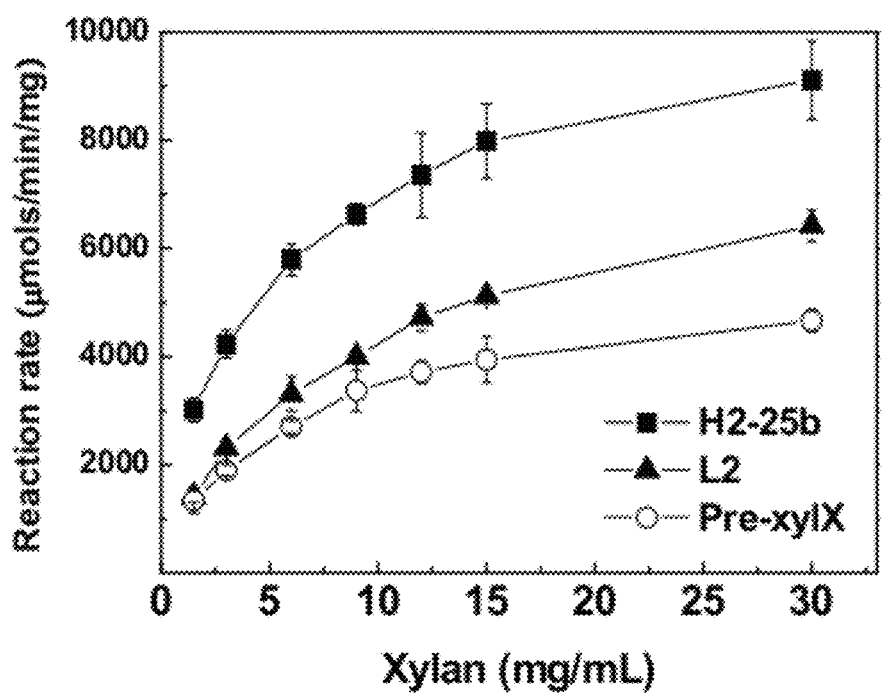
FIG. 6 is a graph showing the reaction rates of Pre-xylX, XylX-L2 and XylX-H2-25b.

The effect of xylan concentration on the reaction rates of reducing sugar released by XylX-H2-25b, XylX-L2, and pre-XylX was determined. See FIG. 6. Derived from data shown in FIG. 6, the kinetic parameters of the mutant xylanases at 60° C., pH 7, are listed in Table 4 below. The highest $V_{max}$, $K_m$ and $k_{cat}$ values of XylX-H2-25b demonstrate its superiority in every aspect. A different behavior was exhibited by the mutant XylX-L2: although the rates of reducing sugar release was higher than the one of pre-XylX at the overall range of xylan concentrations, the $K_m$ of mutant XylX-L2 was the largest at 19.23±3.62 mg/mL.

TABLE 4

Kinetic parameters of XylX-H2 and XylX-L2 at 60° C., pH 7.

| Xylanase | $V_{max}$ (μmol/min mg) | $K_m$ (mg/mL) | $k_{cat}$ (1/s) |
|---|---|---|---|
| H2-25b | 11688.02 ± 504.74 | 3.87 ± 0.39 | 8526.46 |
| L2 | 6642.27 ± 961.22 | 19.23 ± 3.62 | 2780.68 |
| Pre-XylX[a] | 4952.56 ± 72.87 | 6.78 ± 0.59 | 2770.54 |

[a]data described in Ko et al., Bioresour Technol. 101: 7882-7888, 2010.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated polypeptide comprising an amino acid sequence that is at least 90% identical to the amino acid sequence of SEQ ID NO:2, wherein the polypeptide includes an Ala at a position that corresponds to residue 44 of the amino acid sequence SEQ ID NO:2 and a deletion of two amino acids that correspond to residues 345 and 346 of the amino acid sequence of SEQ ID NO:3, and wherein the polypeptide exhibits a lower optimal temperature and a higher specific activity as compared to a wild-type xylanase from *Paenibacillus campinasensis*.

2. The polypeptide of claim 1, wherein the polypeptide comprises an amino acid sequence that is at least 95% identical to the amino acid sequence of SEQ ID NO:2.

3. The polypeptide of claim 1, wherein the polypeptide comprises the amino acid sequence of SEQ ID NO:2.

4. The polypeptide of claim 1, wherein the polypeptide further comprises a His tag.

5. The polypeptide of claim 3, wherein the polypeptide further comprises a His tag at the C-terminus.

6. A method of degrading xylan, the method comprising providing the polypeptide of claim 1, and mixing xylan and the polypeptide.

7. The method of claim 6, wherein the polypeptide comprises the amino acid sequence of SEQ ID NO:2.

* * * * *